United States Patent [19]

Heubach

[11] 4,087,535

[45] May 2, 1978

[54] 5-METHYL-ISOXAZOLE-4-CARBOXYLIC ACID ANILIDES

[75] Inventor: Günther Heubach, Kelkheim, Taunus, Germany

[73] Assignee: Hoechst Aktiengesellschaft, Frankfurt am Main, Germany

[21] Appl. No.: 692,306

[22] Filed: Jun. 3, 1976

[30] Foreign Application Priority Data

Jun. 5, 1975 Germany ............................. 2524959

[51] Int. Cl.$^2$ .................... C07D 261/18; A61K 31/42
[52] U.S. Cl. .............................. 424/272; 260/307 H; 260/562 K
[58] Field of Search .................... 424/272; 260/307 H

[56] References Cited

U.S. PATENT DOCUMENTS 2,126,329  8/1938  Hoffer .................................. 260/294
2,288,863  7/1942  Wenner ................................ 260/307

OTHER PUBLICATIONS

Dains et al., J. Am. Chem. Soc. 35, pp. 959, 968 (1913).
Ajello et al., C.A. 81, 120589t (1974).

*Primary Examiner*—Raymond V. Rush
*Attorney, Agent, or Firm*—Curtis, Morris & Safford

[57] ABSTRACT

A 5-methyl-isoxazole-4-carboxylic acid anilide is prepared by heating an acetoacetic acid anilide with an orthoformic acid ester and a carboxylic acid anhydride, isolating the resulting 2-alkoxymethylene-acetoacetic acid anilide and then treating it with hydroxylamine in an organic solvent. The compounds of the invention have anti-inflammatory and analgetic activity.

24 Claims, No Drawings

5-METHYL-ISOXAZOLE-4-CARBOXYLIC ACID ANILIDES

The present invention relates to 5-methyl-isoxazole-4-carboxylic acid anilides of the formula I

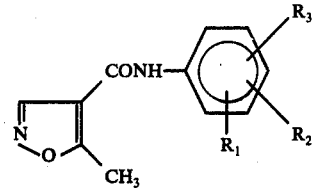

in which $R_1$, $R_2$ and $R_3$, which may be identical or different, each stand for an alkyl group of 1, 2 or 3 carbon atoms, an alkoxy group of 1, 2 or 3 carbon atoms, an alkylthio group of 1, 2 or 3 carbon atoms, which groups may be substituted partly or totally by identical or different halogen atoms, such as fluorine, chlorine, bromine or iodine atoms; for halogen atoms, such as fluorine, chlorine, bromine or iodine atoms, for nitro, cyano, alkoxycarbonyl groups of 1, 2 or 3 carbon atoms in the alkyl moiety, and in which $R_1$ and $R_2$ each further stands for hydrogen, in which case, however, $R_3$ cannot stand for methyl but additionally can stand for a phenyl group which may carry one or two fluorine, chlorine, bromine or iodine atoms, alkyl groups of 1, 2 or 3 carbon atoms or alkoxy groups of 1, 2 or 3 carbon atoms, or for a phenoxy group which may carry one or two fluorine, chlorine, bromine or iodine atoms, alkyl groups of 1, 2 or 3 carbon atoms or alkoxy groups of 1, 2 or 3 carbon atoms, or in which $R_1$ stands for hydrogen, and $R_2$ and $R_3$ together stand for a methylene-dioxy group or together with the phenyl ring, to which they are linked, they stand for a naphthalene ring.

Preferred are compounds of formula I, in which $R_1$ and $R_2$ each stands for hydrogen, $R_3$ for halogen, such as a fluorine, chlorine, or bromine atom, the $CF_3$-group, an alkoxy group of 1 or 2 carbon atoms which may be substituted partly or entirely by identical or different halogen atoms, especially by fluorine or chlorine atoms.

Furthermore preferred are compounds of formula I in which $R_1$ stands for hydrogen, $R_2$ and $R_3$, which may be identical or different, each stand for halogen, such as a chlorine, fluorine or bromine atom, or the $CF_3$-group.

Still further preferred are compounds of formula I, in which $R_1$ stands for hydrogen, $R_2$ for an alkyl group of 1 or 2 carbon atoms and $R_3$ for a halogen atom, such as a fluorine, chlorine or bromine atom.

More specifically preferred is a compound of the formula I, in which $R_1$ stands for hydrogen, and $R_2$ and $R_3$ together form the 3,4-methylene-dioxy group.

The present invention further relates to a process for the manufacture of the compounds of formula I, which comprises heating an acetoacetic acid anilide of the formula II

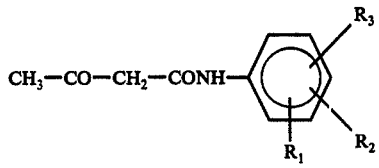

in which $R_1$, $R_2$ and $R_3$ have the meaning given above, with an advantageously at least equimolar amount of an orthoformic acid ester of the formula III $$HC(OR)_3 \qquad (III)$$

in which R stands for an alkyl group of 1 to 4 carbon atoms, preferably methyl or ethyl, and advantageously with a 2- to 4-fold molar excess amount of a carboxylic acid anhydride, advantageously an aliphatic carboxylic acid anhydride having 2 to 6 carbon atoms, preferably acetic anhydride, for 30 minutes to 3 hours to a temperature of from 80° to 150° C, preferably to the boiling point of the mixture, isolating the resulting 2-alkoxymethylene-acetoacetic acid anilide of the general formula IV

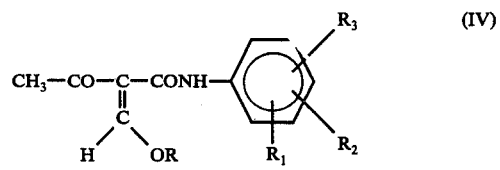

in which R, $R_1$, $R_2$ and $R_3$ have the meaning given above, and then treating this compound with an advantageously at least equimolar amount of hydroxyamine in an organic solvent or mixture of solvents, preferably methanol, ethanol, propanol or isopropanol, optionally with the addition of up to 2 parts by volume, preferably up to 1 part by volume, of water per part by volume of organic solvent, at a temperature of from 0° to 100° C, preferably from 10° to 50° C.

The 2-alkoxymethylene-acetoacetic acid anilides of formula IV required for the manufacture of the compounds of formula I as starting material are new compounds.

Merely the preparation of the 2-ethoxymethylene-acetoacetic acid anilide, which is outside the scope of this invention, from acetoacetic acid anilide, orthoformic acid triethyl ester and acetic anhydride has been described by G. Kempter, W. Schmidt and H. Dost, Chem. Ber. 98, 955 to 961 (1965).

Table 1 comprises the new 2-ethoxymethylene-acetoacetic acid anilides.

The isoxazoles of formula I of this invention are new compounds. Merely three analogues of the isoxazoles, in which $R_1$, $R_2$ and $R_3$ stand for hydrogen, or $R_1$ and $R_2$ stand for hydrogen and $R_3$ for 2-$CH_3$ or 4-$CH_3$, have been described by F. B. Dains and E. L. Griffin, J. Am. Chem. Soc. 35, 959 to 976 (1913). Those known compounds, however, have no practically useful anti-inflammatory or analgetic properties.

The reaction step starting from a compound of formula IV to yield the compound of formula I is surprising. It comprises cyclisation of the easily obtainable 2-ethoxymethylene-acetoacetic acid anilides with hydroxylamine to provide the isoxazoles of formula I already at room temperature with a yield of from 90 to 100%.

The new compounds of formula I are listed in Table 2.

The compounds of formula I of the invention exhibit strong anti-inflammatory and analgetic properties. Having about the same anti-inflammatory effect, they have substantially lower toxicity levels than the known phenylbutazone, or at about the same toxicity level they exhibit a better activity.

Moreover, their analgetic effect is superior to that of phenylbutazone, and their ulcerogenic side effect is substantially weaker than that of phenylbutazone.

Their anti-inflammatory effect was demonstrated on adjuvant arthritis in rats (Pearson, C. M. and Wood, F. D., Arthrit. Rheumat., 2 (1959), 440) and their analgetic effect was demonstrated by means of the writhing test in mice (Sigmund, E. et al., Proc. Soc. Exp. Biol. Med. 95 (1957), 729).

The $ED_{50}$ levels were determined graphically on probability paper. In the writhing test, the $ED_{50}$ is defined to be the dose of active ingredient that reduces the number of writhings by 50% as compared to a control group. In the adjuvant arthritis test, the effect was judged by observing the inhibition in the secondary lesions, which the animals inflicted to their ears, paws and tails, on the 17th day after administration of the active ingredient compositions had started, in comparison with the control group. $ED_{50}$ is considered the dose that reduces these lesions by 50% as compared to those of the control group.

To examine the ulcerogenic activity, the substances to be tested were orally administered to male rats of a Sprague-Dawley strain that had been kept unfed for 18 hours. 24 hours after administration, the gastrointestinal tract of the animals was inspected for ulcers.

In a test for the acute toxicity according to Litchfield and Wilcoxon (Litchfield, J. T. And Wilcoxon, F. W., J. Pharmacol. exp. Ther. 96 (1949), 99), the $LD_{50}$ levels were determined in male or female N.M.R.I. mice or in female Wister-Lewis rats.

The data found for some compounds of formula I and for the known phenylbutazone are listed in the following Table 3.

$C_{13}H_{13}Cl_2NO_3$ molecular weight 302.15 Calculated: C 51.7%; H 4.3%; N 4.6% Found: C 51.8%; H 4.1%; N 4.5%

In an analogous manner, the compounds listed in Table 1 were prepared. In the case of readily soluble 2-ethoxymethylene-acetoacetic acid anilides, the reaction mixture must, under certain circumstances, be concentrated by distillation.

(b) 5-Methyl-isoxazole-4-carboxylic acid-3,4-dichloro-anilide of formula I 0.11 mol (7.65 g) of hydroxy-amine hydrochloride was dissolved in 30 ml of water, an ice-cold solution of 0.11 mol of sodium hydroxide (4.4 g) in 20 ml of water was added, and the mixture was diluted with 150 ml of methanol. Then, 0.1 mol (30.2 g) of the 2-ethoxymethyleneacetoacetic acid-3,4-dichloro-anilide obtained according to a) was added, and the mixture was stirred for about 4 hours at room temperature. The solution was then cooled to +5° C, the crystals were suction-filtered and washed with water. After drying in air, colorless crystals were obtained. The yield amounted to 26.4 g, corresponding to 97.5% of the theoretical yield of 5-methyl-isoxazole-4-carboxylic acid-3,4-dichloroanilide. Melting point after recrystallization from methanol: 146° C.

$C_{11}H_8Cl_2N_2O_2$ molecular weight 271.1 Calculated: C 48.7%; H 3.0%; N 10.3% Found: C 48.6%; H 3.0%; N 10.2%

In an analogous manner, the compounds listed in Table 2 were prepared.

TABLE 1

| Nr. | Intermediate products of formula IV: | | | melting point (° C) |
|---|---|---|---|---|
| | $R_1$ | $R_2$ | $R_3$ | |
| 1 | H | H | 2-Cl | 95–96 |
| 2 | H | H | 3-Cl | 98 |
| 3 | H | H | 4-Cl | 139.5 |

TABLE 3

| Substance No. from Table 2 | $ED_{50}$ in mg/kg per os | | $LD_{50}$ in mg/kg per os[1] | | Limit dose in mg/kg per os without ulcerogenic activity |
|---|---|---|---|---|---|
| | writhing test | adjuvant arthritis | mice | rats | |
| 6 | <60 | 24 | 1280 (780 – 2099) | 920 (826 – 1025) | 100 |
| 12 | 25 – 40 | 42 | 2530 (2162 – 2960) | — | — |
| 8 | ca. 60 | <100 | 2330 (1752 – 3099) | >3150 | ≧400 |
| 21 | <60 | <100 | 300 – 100[2] | — | — |
| Phenyl-butazone | 60 – 100 | 37 | 1145 (939–1397) | 780 (675 – 901) | 63 |

[1] Limits of confidence for p = 0.05 in brackets Observation time 7 days
[2] administered by the intraperitoneal route The following Examples illustrate the invention.

EXAMPLE 1:

(a) 2-Ethoxymethylene-acetoacetic acid-3,4-dichloro-anilide of formula IV 1.0 Mol of acetoacetic acid-3,4-dichloro-anilide of formula II (246 g) is refluxed with 1.12 mols of orthoformic acid triethyl ester of formula III (166 g) and 2.97 mols of acetic anhydride (302 g) for 1.5 hours. After cooling to room temperature, the precipitated crystals are suction-filtered and washed with a mixture of 1 part by volume of benzene and 2 parts by volume of gasoline. The yield amounts to 251 g, corresponding to 83% of the theoretical yield of 2-ethoxymethylene-acetoacetic acid-3,4-dichloro-anilide. Melting point after recrystallization from benzene: 125° to 126° C.

| 4 | H | 2-Cl | 4-Cl | 127 |
|---|---|---|---|---|
| 5 | H | 2-Cl | 5-Cl | 146 |
| 6 | H | 3-Cl | 4-Cl | 125–126 |
| 7 | H | 3-Cl | 5-Cl | 131 |
| 8 | H | H | 3-Br | 118 |
| 9 | H | H | 4-Br | 124 |
| 10 | H | H | 4-F | 127 |
| 11 | H | H | 3-CF$_3$ | 84 |
| 12 | H | 3-CF$_3$ | 5-CF$_3$ | 111 |
| 13 | H | H | 4-NO$_2$ | 160–162 |
| 14 | H | H | 3-OCF$_2$—CHF$_2$ | 73–74 |
| 15 | H | H | 3-CH$_3$ | 73 |
| 16 | H | 2-CH$_3$ | 4-CH$_3$ | 105 |
| 17 | H | H | 2-OCH$_3$ | 94–95 |
| 18 | H | H | 3-OCH$_3$ | 88 |
| 19 | H | H | 4-OCH$_3$ | 94 |
| 20 | H | H | 2-OC$_2$H$_5$ | 110 |
| 21 | H | H | 3,4—O\\CH$_2$/—O | 136–137 |
| 22 | H | H | 4-COOC$_2$H$_5$ | 137–138 |

TABLE 1-continued

Intermediate products of formula IV:

| Nr. | R₁ | R₂ | R₃ | melting point (° C) |
|---|---|---|---|---|
| 23 | H |  | 2,3 —C(=CH—CH=C—) | 126 |
| 24 | H | 2-CH₃ | 3-Cl | 129 |
| 25 | H | 2-CH₃ | 4-Cl | 128 |
| 26 | H | 2-CH₃ | 5-Cl | 141 |
| 27 | H | 2-CF₃ | 4-Cl | 108 |
| 28 | H | H | 4—O—⟨C₆H₄⟩—Cl | 78–79 |
| 29 | H | H | 4—O—⟨C₆H₄⟩—Br | 88 |
| 30 | H | H | 2—⟨C₆H₅⟩ | 113–114 |
| 31 | H | H | 3-OCF₂—CHClF | 62 |
| 32 | H | H | 3-SCH₃ | 92 |
| 33 | H | 2-Br | 5-Br | 140 |
| 34 | H | 3-Cl | 4-CH₃ | 120 |
| 35 | H | H | 3-J | 148 |
| 36 | H | H | 3-CN | 106.5 |
| 37 | H | 2-CH₃ | 5-Br | 140–141 |
| 38 | H | 3-CH₃ | 4-Br | 123 |
| 39 | H | H | 3-F | 109.5 |
| 40 | H | 2-CH₃ | 3-F | 124 – 125 |
| 41 | H | 3-Cl | 4-F | 110.5 – 111.5 |
| 42 | H | 3-CF₃ | 4-Cl | 115.5 |
| 43 | H | H | 4-SCH₃ | 116 – 118 |
| 44 | 2-OCH₃ | 5-OCH₃ | 4-Cl | 154.5 – 156 |
| 45 | H | 2-F | 5-CF₃ | 139.5 – 140 |
| 46 | 2-F | 4-F | 5-Cl | 138 |
| 47 | H | H | I | 148.5 – 149 |
| 48 | H | 2-OCH₃ | 4-OCH₃ | 142 – 142.5 |
| 49 | H | 2-OCH₃ | 5-OCH₃ | 116 |

TABLE 2

5-Methyl-isoxazole-4-carboxylic acid anilides of formula I

| No. | R₁ | R₂ | R₃ | melting point (° C) |
|---|---|---|---|---|
| 1 | H | H | 2-Cl | 111–112 |
| 2 | H | H | 3-Cl | 106–107 |
| 3 | H | H | 4-Cl | 151 |
| 4 | H | 2-Cl | 4-Cl | 120–121 |
| 5 | H | 2-Cl | 5-Cl | 122 |
| 6 | H | 3-Cl | 4-Cl | 146 |
| 7 | H | 3-Cl | 5-Cl | 182–183 |
| 8 | H | H | 3-Br | 122 |
| 9 | H | H | 4-Br | 162–163 |
| 10 | H | H | 4-F | 117–118 |
| 11 | H | H | 3-CF₃ | 119–120 |
| 12 | H | 3-CF₃ | 5-CF₃ | 176 |
| 13 | H | H | 4-NO₂ | 190–191 |
| 14 | H | H | 3-OCF₂—CHF₂ | <40 |
| 15 | H | H | 3-CH₃ | 80–81 |
| 16 | H | 2-CH₃ | 4-CH₃ | 160–161 |
| 17 | H | H | 2-OCH₃ | 81.5 |
| 18 | H | H | 3-OCH₃ | 92–93 |
| 19 | H | H | 4-OCH₃ | 133–134 |
| 20 | H | H | 2-OC₂H₅ | 105–106 |
| 21 | H | H | 3,4—O—CH₂—O | 125–126 |
| 22 | H | H | 4-COOC₂H₅ | 167.5 |
| 23 | H |  | 2,3 —C(=CH—CH=C—H) | 137–138 |
| 24 | H | 2-CH₃ | 3-Cl | 158–159 |
| 25 | H | 2-CH₃ | 4-Cl | 147–148 |
| 26 | H | 2-CH₃ | 5-Cl | 127–128 |
| 27 | H | 2-CF₃ | 4-Cl | 133–134 |
| 28 | H | H | 2—⟨C₆H₅⟩ | 116–117 |
| 29 | H | H | 4—O—⟨C₆H₄⟩—Cl | 137–138 |

TABLE 2-continued

5-Methyl-isoxazole-4-carboxylic acid anilides of formula I

| No. | R₁ | R₂ | R₃ | melting point (° C) |
|---|---|---|---|---|
| 30 | H | H | 4—O—⟨C₆H₄⟩—Br | 138 |
| 31 | H | H | 3-OCF₂—CHClF | 73.5–74.5 |
| 32 | H | H | 3-SCH₃ | 71–72 |
| 33 | H | 2-Br | 5-Br | 171–173 |
| 34 | H | 3-Cl | 4-CH₃ | 149–150 |
| 35 | H | H | 3-I | 148–149 |
| 36 | H | H | 3-CN | 199.5–200.5 |
| 37 | H | 2-CH₃ | 5-Br | 138–139 |
| 38 | H | 3-CH₃ | 4-Br | 130–131 |
| 39 | H | H | 3-F | 122 |
| 40 | H | 2-CH₃ | 3-F | 142 |
| 41 | H | 3-Cl | 4-F | 123 – 124 |
| 42 | H | 3-CF₃ | 4-Cl | 161 – 161.5 |
| 43 | H | H | 4-SCH₃ | 135.5 – 136.5 |
| 44 | 2-OCH₃ | 5-OCH₃ | 4-Cl | 136 – 137.5 |
| 45 | H | 2-F | 5-CF₃ | 107 – 108 |
| 46 | 2-F | 4-F | 5-Cl | 127 |
| 47 | H | H | 4-I | 173 – 173.5 |
| 48 | H | 2-OCH₃ | 4-OCH₃ | 133.5 – 134 |
| 49 | H | 2-OCH₃ | 5-OCH₃ | 87.5 – 88 |

I claim:
1. A 5-methyl-isoxazole-4-carboxylic acid anilide of the formula

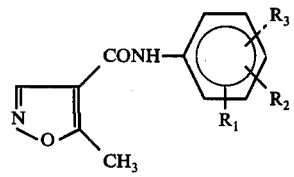

wherein
(A) $R_1$ and $R_2$ are each hydrogen and $R_3$ is halogen, —$CF_3$, alkoxy having 1 or 2 carbon atoms, or halo-substituted alkoxy having 1 or 2 carbon atoms;
(B) $R_1$ is hydrogen and $R_2$ and $R_3$, which are the same or different, are halogen or —$CF_3$;
(C) $R_1$ is hydrogen, $R_2$ is alkyl having 1 or 2 carbon atoms, and $R_3$ is halogen; or
(D) $R_1$ is hydrogen and $R_2$ and $R_3$ are 3′,4′- methylene dioxy.

2. A compound as in claim 1 (A).
3. A compound as in claim 1 (B).
4. A compound as in claim 1 (C).
5. A compound as in claim 1 (D).
6. A pharmaceutical composition comprising an effective amount of a compound as in claim 1 in combination with a pharmaceutically acceptable carrier.
7. The method of combatting pain and/or inflammation which comprises administering an effective amount of a compound as in claim 1 to a patient in need of such treatment.
8. A compound as in claim 2 which is 5-methyl-isoxazole-4-carboxylic acid 4-fluoroanilide.
9. A compound as in claim 2 which is 5-methyl-isoxazole 4-carboxylic acid 4-chloroanilide.
10. A compound as in claim 2 which is 5-methyl-isoxazole-4-carboxylic acid 4-bromoanilide.
11. A compound as in claim 2 which is 5-methyl-isoxazole 4-carboxylic acid 4-iodoanilide.
12. A compound as in claim 2 which is 5-methyl-isoxazole-4-carboxylic acid 3-trifluoromethylanilide.
13. A compound as in claim 3 which is 5-methyl-isoxazole-4-carboxylic acid 3,4-dichloroanilide.

14. A compound as in claim 3 which is 5-methyl-isoxazole-4-carboxylic acid 3,5-bis-trifluoromethyl anilide.

15. A compound as in claim 3 which is 5-methyl-isoxazole-4-carboxylic acid 3- chloro-4-fluoroanilide.

16. A compound as in claim 3 which is 5-methyl-isoxazole-4-carboxylic acid 3-trifluoromethyl-4-chloroanilide.

17. A compound as in claim 3 which is 5-methyl-isoxazole-4-carboxylic acid 2-fluoro-5-trifluoromethyl anilide.

18. A compound as claim 4 which is 5-methyl-isoxazole-carboxylic acid 2-methyl-3-chloroanilide.

19.

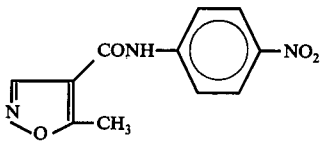

20. A pharmaceutical composition comprising an effective amount of the compound of claim 19 in combination with a pharmaceutically-acceptable carrier.

21. The method of combatting pain and/or inflammation which comprises administering an effective amount of the compound of claim 19 to a patient in need of such treatment.

22.

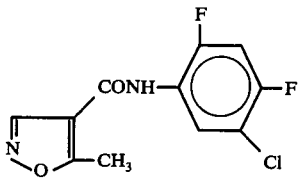

23. A pharmaceutical composition comprising an effective amount of the compound of claim 22 in combination with a pharmaceutically acceptable carrier.

24. The method of combatting pain and/or inflammation which comprises administering an effective amount of the compound of claim 22 to a patient in need of such treatment.

* * * * *